United States Patent [19]
Collins, Jr.

[11] 4,085,618
[45] Apr. 25, 1978

[54] COMPOSITE SAMPLING SYSTEM AND ROTATABLE SAMPLING VALVE THEREFOR

[75] Inventor: Henry R. Collins, Jr., Livingston, Tex.

[73] Assignee: Collins Products Company

[21] Appl. No.: 736,259

[22] Filed: Oct. 27, 1976

[51] Int. Cl.² .............................................. G01N 1/20
[52] U.S. Cl. ................................. 73/422 TC; 137/242
[58] Field of Search .................. 73/422 TC; 137/242; 251/360

[56] References Cited
U.S. PATENT DOCUMENTS

| | | | |
|---|---|---|---|
| 2,217,855 | 10/1940 | Bassler | 73/422 TC |
| 2,679,377 | 5/1954 | Mueller | 251/360 |
| 3,080,759 | 3/1963 | McQwaid | 73/422 TC |

*Primary Examiner*—S. Clement Swisher
*Attorney, Agent, or Firm*—Pravel, Wilson & Gambrell

[57] ABSTRACT

A sampling system for obtaining composite samples of flow streams is provided. The system includes a rotatable sampling valve which periodically removes a fixed sample volume from the stream for storage in a sample container.

6 Claims, 4 Drawing Figures

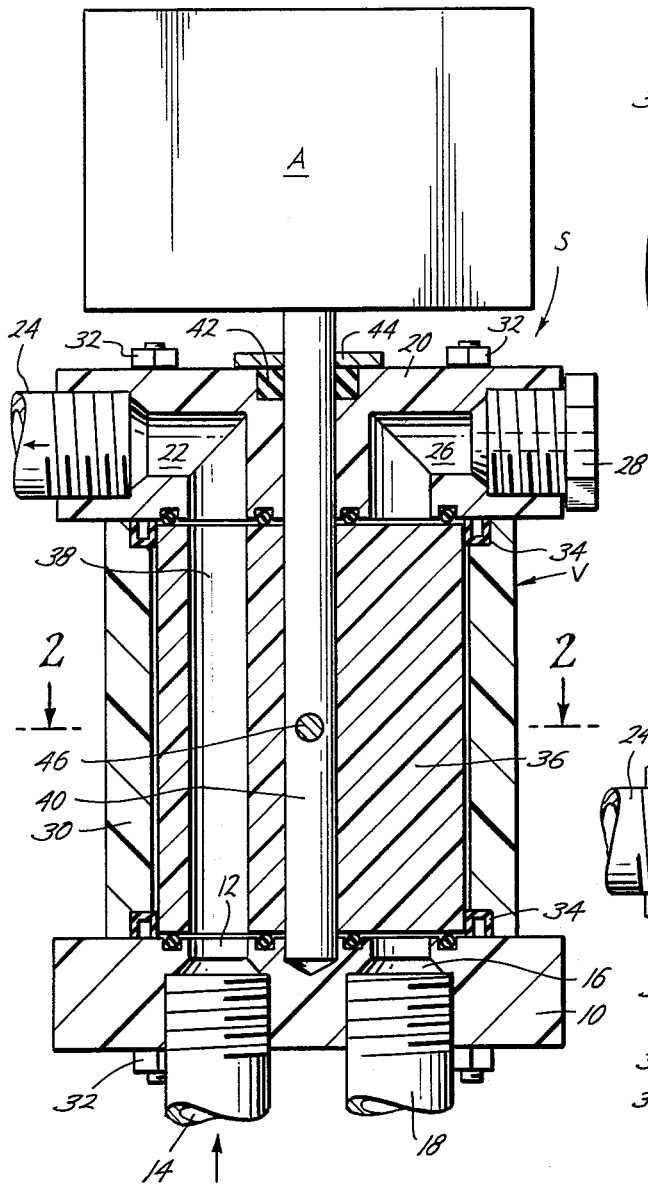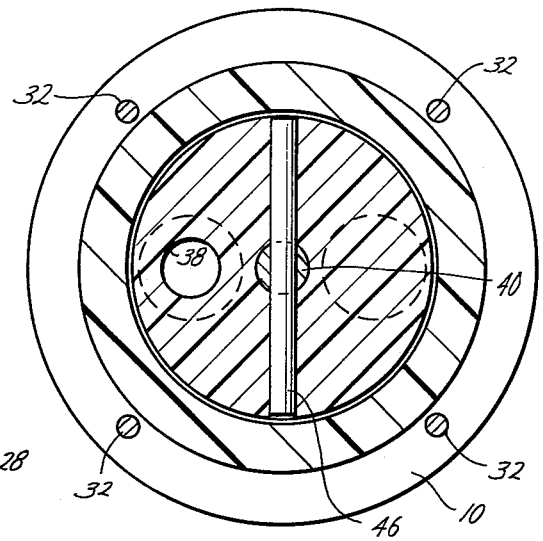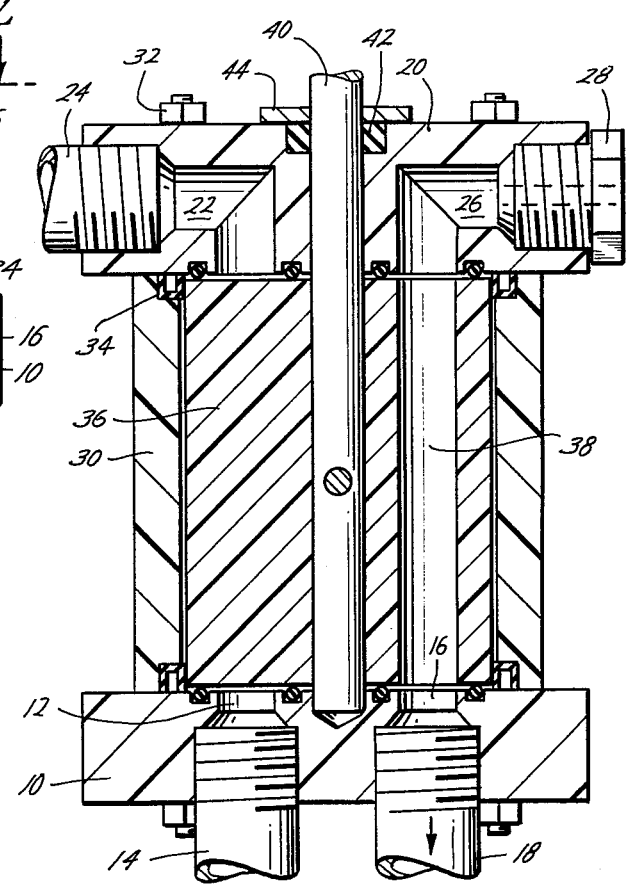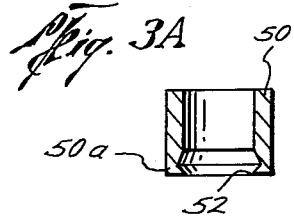

COMPOSITE SAMPLING SYSTEM AND ROTATABLE SAMPLING VALVE THEREFOR

BACKGROUND OF THE INVENTION

1. Field of Invention

The present invention relates to composite sampling systems and sampling valves therefor.

2. Description of Prior Art

Composite sampling systems, such as in U.S. Pat. No. 3,798,972 of Applicant, have been used to extract samples of fluid from conduit systems.

Rotatable or rotary valves are also known, as evidenced by U.S. Pat. Nos. 31,530; 2,314,031; 2,413,293; 3,195,776; 3,251,511; 3,403,827; and 3,506,237. However, certain of these valves were for insertion of solids into conduits, rather than sample removal. Others of these valves were for handling of solid matter and were specifically designed to prevent damage to the solid matter during valve operation.

However, in obtaining composite samples of effluent materials, two further considerations existed. First, an accurate sample of a fixed, predetermined volume must be repeatedly taken at particular intervals over a sampling operation period. Second, suspended matter or debris in the conduit system must not interfere with operation of the sampling system or vary the sample volume.

SUMMARY OF THE INVENTION

Briefly, the present invention provides a new and improved composite sampling system having a rotary valve to obtain fixed predetermined volumes of sample fluid in a conduit stream. The rotary valve of the sampling system has a rotatable sampling member movable between a normal position aligned with the conduit stream and a sampling outlet position aligned with a fluid conductor leading to a sample storage container. A sample passage is formed in the sampling member having a volume corresponding to the desired sample volume. The sample passage is generally aligned with the conduit stream and moves to the sampling position in response to a valve actuator. Inlet and outlet portions of the sample passage and of the conduit stream and fluid conductor are provided with rigid inserts to shear debris in the conduit stream when the sampling valve member is moved to prevent interference with valve operation or variance in sample volume.

BRIEF DESCRIPTION OF THE DRAWINGS

FIG. 1 is an elevation view, taken partly in cross-section, of a sampling system according to the present invention in a first operating position;

FIG. 2 is a cross-sectional view taken along the lines 2—2 of FIG. 1;

FIG. 3 is another elevation view of the system of FIG. 1, in a different operating position; and FIG. 3A is a cross-sectional view of a shearing sleeve insert used in the system of FIG. 1.

DESCRIPTION OF THE PREFERRED EMBODIMENT

In the drawings, the letter S designates generally the composite sampling system of the present invention. The system S includes a sampling valve V which, in a manner to be set forth, periodically obtains a sample of predetermined volume. The fluid being sampled may be, for example, effluent from an industrial facility, such as a chemical plant or refinery, or sewage in a municipal sewage treatment system. The effluent is typically monitored over a fairly long period of time for pollution control purposes.

The system S includes a base plate member 10 of the valve V which has a process stream inlet port 12 formed therein. The process stream inlet port 12 has a threaded surface formed therein for receipt of a process stream inlet conduit 14. The base plate member 10 further has a transfer port 16 formed therein which also includes a threaded surface portion to receive a transfer conduit 18 by which the sample obtained in the valve V, in a manner to be set forth below, is transferred to a conventional sample container which may be refrigerated, if desired.

The valve V further includes a cap plate member 20 having an outlet port 22 formed therein with a threaded surface which receives an outlet conduit 24 carrying the fluid stream away from the system S. A sample pressure inlet port 26 is formed in the cap plate member 20 and permits, where desired, fluid under pressure to be admitted to purge the sample from the valve V in a manner to be set forth. If pressurized fluid is not required, inlet port 26 is vented through a conventional hollow tube fitting 28 to atmospheric pressure to assist in purging the sample from the valve V.

The valve V further includes a cover sleeve member 30 mounted between the base plate member 10 and cap plate member 20 by bolts 32 or other suitable attaching means. Annular sealing gaskets 34 are mounted in suitable recesses at the upper and lower ends of the cover sleeve member 30 to provide a seal between the upper and lower ends of the sleeve 30 and the cap plate member 20 and base plate member 10, respectively.

The valve V further includes a rotary or rotatable cylindrical sampling body member 36 mounted within the sleeve 30. The sampling body member 36 has a sample receiving passage or tube 38 formed therein which is normally aligned in a first or normal position (FIG. 1) between the inlet port 12 and outlet port 22. The sample receiving tube 38 is of a fixed, predetermined size so that continually retained therein is a fixed, predetermined volume of a sample of the flow stream passing from the conduit 14 through the sampling system S of the present invention.

The sampling body member 36 has a central longitudinal opening formed therein in alignment with similar openings in the cap plate member 20 and base plate member 10 for receipt of an actuator rod 40 which moves in response to a valve actuator A, which may be any of several suitable commercially available valve actuators. The actuator A may be controlled by a process control computer or other suitable control means, or may be manually operable, if desired. A gasket 42 and cover plate 44 are mounted in the cap plate member 20 adjacent the actuator rod 40 for sealing purposes. O-rings or other suitable sealing means are formed adjacent each of the ports 12, 16, 22 and 26 for providing a seal between the valve body member 36 and the base plate member 10 and cap plate member 20.

A link pin 46 extends through a transverse opening in the valve member 36 and actuator rod 40 to interconnect the valve member 36 and rod 40 so that the valve member 36 may be rotated and moved from the first position (FIG. 1) with the sample receiving tube aligned with the inlet port 12 and outlet port 22 to a second or sampling outlet position (FIG. 3) with the sample receiving tube aligned with the transfer port 16 to transfer the sample from the tube 38 through the conduit 18 to the sample container. As has previously been set forth, where a particularly viscous or thick fluid is being sampled by the system S, fluid under pressure may be admitted through the port 26 aligned with the port 16 in order to assist in purging the sample volume in the sample tube 38 through the transfer port 16.

Where debris, such as strings and solids, is present in the fluid being sampled by the system S, the operation of the valve V can be hampered by such debris, and further, the volume of the sample obtained from the sample receiving tube 38 reduced. Accordingly, metal inserts 50 are provided. The inserts 50 would be used in each of the ports 12, 16, 22 and 26 by being mounted in suitable sockets formed adjacent such ports. Further, the inserts are mounted at the upper and lower ends of the sample receiving tube 38 in suitable recessed sockets. The inserts 50 (FIG. 3A) are formed from a suitably hard metal such as stainless steel and have an inclined cutting edge 52 formed adjacent and about the periphery an end 50a along which shearing of the debris in the process stream is to take place. The cutting edge 52 is formed along a straight-honed edge in order to prevent damage to the O-rings adjacent the ports in the valve V.

In the operation of the present invention, the flow stream being sampled by the system S enters the valve V through the conduit 14 at ports 12 and flows through the sample receiving tube 38 to the outlet port 22 and conduit 24, continuously purging tube 38 while simultaneously retaining a fixed, sample volume therein. At predetermined times, upon instruction from a process control computer or manual operation by an equipment operator, the actuator A is energized, causing the cylindrical valve member 36 to rotate from the first position (FIG. 1) to the second position (FIG. 3). As the valve member 36 is rotated, the inlet port 12 and outlet port 22 are blocked to prevent leakage into the sample container from the system S. The valve member 36 rotates in response to the actuator A from the first position to the second position allowing the predetermined sample volume in the sample receiving tube 38 to flow, either under the influence of gravity or in response to pressure from port 26 through the transfer port 16 and conduit 18 to the sample container. After a suitable period of time, typically ten seconds, the valve 36 rotates again to the first position (FIG. 1).

The foregoing disclosure and description of the present invention is illustrative and explanatory thereof and various changes in the size, shape, and materials as well as in the details of the preferred embodiment may be made without departing from the spirit of the invention.

I claim:

1. A composite sampling system for obtaining composite samples from a flow stream, comprising:
   (a) an inlet conduit for the flow stream;
   (b) sampling valve means in fluid communication with said inlet conduit, said sampling valve means comprising:
      (1) a base plate member having an inlet port for receiving fluid from said inlet conduit;
      (2) a cap plate member having an outlet port for transferring fluid from said sampling valve means;
      (3) a transfer port for transferring samples obtained by said sampling valve means;
      (4) a sampling body member mounted between said base plate member and said cap plate member;
      (5) said sampling body member having a sample receiving tube formed therein;
      (6) said sample receiving tube having a fixed size to receive a predetermined volume of the flow stream therein; and
      (7) said sample receiving tube being normally aligned in a first position between said inlet port and said outlet port for flow of the flow stream therethrough in order to continually retain a sample of predetermined volume therein;
   (c) actuator means for rotationally moving said sampling body member to move said sample receiving tube from said first position to a second position aligning said sample receiving tube with said transfer port to transfer the sample of predetermined volume from said sampling valve means; and
   (d) shearing insert means mounted in said sampling valve means in at least one of said inlet port, said outlet port, said transfer port and said sample receiving tube for shearing debris in the flow stream during movement of said sampling body member; and
   (e) inclined cutting edges formed in said shearing insert means to assist in shearing debris in the flow stream.

2. The structure of claim 1, wherein said shearing insert means are formed in said sampling valve means in each of said inlet port, said outlet port, said transfer port and said sample receiving tube and further including:
   inclined cutting edges formed in each of said shearing insert means to assist in obtaining debris in the flow stream.

3. The structure of claim 1, further including:
   a pressure inlet port aligned with said transfer port for admitting pressurized fluid to purge said sample receiving tube when said tube is in the second position.

4. A sampling valve for a composite sampling system to obtain composite samples from a flow stream, comprising:
   (a) a base plate member having an inlet port for receiving fluid from said inlet conduit;
   (b) a cap plate member having an outlet port for transferring fluid from said sampling valve means;
   (c) a transfer port for transferring samples obtained by said sampling valve means;
   (d) a sampling body member mounted between said base plate member and said cap plate member;
   (e) said sampling body member having a sample receiving tube formed therein;
   (f) said sample receiving tube having a fixed size to receive a predetermined volume of the flow stream therein;
   (g) said sample receiving tube being normally aligned in a first position between said inlet port for flow of the flow stream therethrough in order to continually retain a sample of predetermined volume therein;
   (h) said sampling body member being rotationally movable from said first position to a second position aligning said sample receiving tube with said transfer port to transfer the sample of predetermined volume from the sampling valve;
   (i) shearing insert means mounted in said sampling valve means in at least one of said inlet port, said outlet port, said transfer port and said sample receiving tube for shearing debris in the flow stream during movement of said sampling body member; and (j) inclined cutting edges formed in said shearing insert means to assist in shearing debris in the flow stream.

5. The structure of claim 4, wherein said shearing insert means are formed in said sampling valve means in each of said inlet port, said outlet port, said transfer port and said sample receiving tube and further including: inclined cutting edges formed in each of said shearing insert means to assist in obtaining debris in the flow stream.

6. The structure of claim 4, further including:

a pressure inlet port aligned with said transfer port for admitting pressurized fluid to purge said sample receiving tube when said tube is in the second position.

* * * * *